US008609098B2

(12) United States Patent
Jang et al.

(10) Patent No.: US 8,609,098 B2
(45) Date of Patent: Dec. 17, 2013

(54) COMPOSITION FOR REPRESSION OF HYPERLIPIDEMIA AND OBESITY THROUGH SUPPRESSION OF INTESTINAL CHOLESTEROL ABSORPTION

(75) Inventors: Sang Ho Jang, Yongin-si (KR); Soo Young Choi, Chuncheon-si (KR); Yeom Pyo Lee, Seoul (KR); Jae Jin An, Chuncheon-si (KR); Hong Gul Cheong, Seoul (KR); Hyuck Se Kwon, Chuncheon-si (KR); Jeong Keum Park, Gapyeong-eup (KR); Doo Yeon Baek, Chuncheon-si (KR)

(73) Assignees: Adbiotech Co., Ltd., Chuncheon-Si (KR); Bioceltran Co., Ltd., Chuncheon-Si (KR)

( * ) Notice: Subject to any disclaimer, the term of this patent is extended or adjusted under 35 U.S.C. 154(b) by 0 days.

(21) Appl. No.: 13/579,810

(22) PCT Filed: Apr. 25, 2011

(86) PCT No.: PCT/KR2011/003007
§ 371 (c)(1),
(2), (4) Date: Aug. 17, 2012

(87) PCT Pub. No.: WO2011/155705
PCT Pub. Date: Dec. 15, 2011

(65) Prior Publication Data
US 2012/0322987 A1 Dec. 20, 2012

(30) Foreign Application Priority Data

Jun. 10, 2010 (KR) ........................ 10-2010-0055000

(51) Int. Cl.
*A61K 39/00* (2006.01)
(52) U.S. Cl.
USPC .................. 424/139.1; 424/157.1; 424/172.1; 424/804; 530/389.1; 530/861
(58) Field of Classification Search
None
See application file for complete search history.

(56) References Cited

U.S. PATENT DOCUMENTS 5,367,054 A * 11/1994 Lee ................................. 530/359
2004/0018197 A1* 1/2004 Stafford et al. ............ 424/146.1
2009/0035784 A1* 2/2009 Ioannou et al. ................ 435/7.1

FOREIGN PATENT DOCUMENTS

WO    WO 2004009772 A2 *  1/2004
WO    WO 2005069900 A2 *  8/2005

OTHER PUBLICATIONS

Moreira et al., Nutr Hosp. Oct. 2012;27(5):1408-14. doi: 10.3305/nh.2012.27.5.5887.*
Lucassen et al., Curr Obes Rep. Dec. 2012;1(4):208-215.*
Suzuki et al., Exp Diabetes Res. 2012;2012:824305. doi: 10.1155/2012/824305. Epub Aug. 1, 2012.*
Bray et al., J Am Diet Assoc. May 2005;105(5 Suppl 1):S17-23.*
Stryer, Lubert Biochemistry, $4^{th}$ edition, W.H. Freeman and Company, New York, 1995, pp. 691-703.*
DeSilva, B. et al., "Purified Protein Derivative (PPD) as an Immunogen Carrier Elicits High Antigen Specificity to Haptens", Bioconjugate Chem., 10 (1999), pp. 496-501.
Tini, M. et al., "Generation and application of chicken egg-yolk antibodies," Comparative Biochemistry and Physiology Part A, 131 (2002), pp. 569-574.
Yamanashi, Y., et al., "In-vitro characterization of the six clustered variants of NPC1L1 observed in cholesteral low absorbers", Pharmacogenetics and Genomics, vol. 19, No. 11 (2009), pp. 884-892.
Davies et al "Inactivation of NPC1L1 Causes Multiple Lipid Transport Defects and Protects against Diet-induced Hypercholesterolemia." *Journal of Biological Chemistry.* vol. 280, No. 13, pp. 12710-12720, 2005.
Sane et al "Localization and role of NPC1L1 in cholesterol absorption in human intestine." *Journal of Lipid Research.* vol. 47, pp. 2112-2120, 2006.
Wang et al "Membrane topology of human NPC1 L1, a key protein in enterohepatic cholesterol absorption.." *Journal of Lipid Research.* vol. 50, pp. 1653-1662, 2009.
Yu et al "Cholesterol-regulated Translocation of NPC1L1 to the Cell Surface Facilitates Free Cholesterol Uptake." *Journal of Biological Chemistry.* vol. 281, No. 10, pp. 6616-6624, 2006.

* cited by examiner

*Primary Examiner* — Michael Szperka
(74) *Attorney, Agent, or Firm* — Edwards Wildman Palmer LLP

(57) ABSTRACT

Disclosed are a composition for inhibiting hyperlipidemia and obesity through suppression of intestinal cholesterol absorption. An IgY-type antibody derived from yolk to NPC1L1 (Niemann-Pick C1-Like1), contained, as an active ingredient, in the composition of the present invention is linked to NPC1L1 (Niemann-Pick C1-Like1) that is a cholesterol transport protein in the intestines, thus interfering with binding between cholesterol and the transport protein to completely block absorption of cholesterol in the body and thereby prevent hyperlipidemia and obesity.

2 Claims, 6 Drawing Sheets

1: 373 NPC1L1 recombinant protein
2: 416 NPC1L1 recombinant protein
3: 509 NPC1L1 recombinant proetin
4: KLH conjugated synthetic NPC1L1 peptide 1ˢᵗ Ab ( purified IgY: 2ug/ml O/N at 4°C)
2ⁿᵈ Ab : Anti-chicken IgY (sigma A9046)
  1hr at RT 1:10,000 (recomandation 1:16,000)

COMPOSITION FOR REPRESSION OF HYPERLIPIDEMIA AND OBESITY THROUGH SUPPRESSION OF INTESTINAL CHOLESTEROL ABSORPTION

CROSS-REFERENCE TO RELATED APPLICATIONS

This application is the U.S. national phase, pursuant to 35 U.S.C. §371, of PCT international application Ser. No. PCT/KR2011/003007, filed Apr. 25, 2011, designation the United States and published in Korean on Dec. 15, 2011 as publication WO2011/155705. PCT/KR2011/003007 claims priority to Korean Patent Application Ser. 10-2010-0055000, filed Jun. 10, 2010. The entire contents of the aforementioned patent application are incorporated herein by reference.

SENQUENCE LISTING

The instant application contains a Sequence Listing which has been submitted in ASCII format via EFS-Web and is hereby incorporated by reference in its entirety. Said ASCII copy, created on Aug. 17, 2012, is named 912850_306147.txt and is 29,521 bytes in size.

TECHNICAL FIELD

The present invention relates to a composition for inhibiting hyperlipidemia and obesity. More specifically, the present relates to a composition for inhibiting hyperlipidemia and obesity through suppression of intestinal cholesterol absorption.

BACKGROUND ART

Cholesterol is known to be a factor that induces coronary cardiovascular diseases which are known to be 30% or more of all causes of death at present.

Cardiovascular diseases are considered to be diseases of developing countries having high fat intake and high obesity population and the onset rate thereof in Korea is rapidly increasing due to westernization of diet, lack of exercise, overwork and the like in accordance with development of economical level. In particular, low-density lipoprotein (LDL) that is involved in transport of cholesterol in blood is regarded as a specific arteriosclerosis-inducing factor and oxidized LDL is known to exhibit potent arteriosclerosis induction activity.

Meanwhile, obesity is commonly referred to as a phenomenon in which residual calories left after indigestion and consumption are converted into adipocyte and are deposited in various body sites, in particular, subcutaneous tissues and the abdominal cavity. The causes of obesity include genetic factors, environmental factors, energy metabolic disorders and the like. The types of obesity may be classified into simple (primary) obesity and symptomatic (secondary) obesity depending on the onset cause thereof.

The most of obesity patients suffers from simple (primary) obesity and is known to be caused by accumulation of surplus energy in fat due to calorie over-uptake and consumption lack of calorie in the body thereof.

Symptomatic (secondary) obesity is known to result from diseases such as hypothyroidism, adrenocortical hormone over-secretion and polycystic ovary syndrome, or drugs such as oral contraceptives, tranquilizers, steroid hormones, drugs containing an antihistamine ingredient and the like.

Obesity causes constipation, dyspepsia, gastroenteric troubles due to abdominal press by fat tissues, induces adult diseases such as diabetes, hypertension, arteriosclerosis, cardiac diseases and cancers, and complications thereof as well as mental diseases such as dissatisfaction associated with the body, anxiety, personality disorders and depression. That is, obesity is a cause of all kinds of diseases.

Accordingly, it is necessary to reduce the amount of cholesterol absorbed in the body and thereby prevent cardiovascular diseases and obesity that is a cause of all kinds of diseases. For this purpose, blocking of cholesterol absorption is the most efficient method.

Meanwhile, Ezetimibe is known in the art to be a compound that inhibits absorption of cholesterol, which is also called "Zetia". Taking into consideration the market associated with obesity that gradually increases in demand, development of novel alternative substances is required.

DISCLOSURE

Technical Problem

Therefore, the present invention has been made in view of the above problems, and it is one object of the present invention to develop and provide a composition that is capable of inhibiting or preventing hyperlipidemia and obesity by reducing the amount of cholesterol that is absorbed in the intestines.

Technical Solution

In accordance with one aspect of the present invention, provided is a composition for inhibiting absorption of cholesterol comprising, as an active ingredient, an IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein.

In accordance with another aspect of the present invention, provided is a composition for preventing or inhibiting obesity comprising, as an active ingredient, an IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein.

In accordance with yet another aspect of the present invention, provided is a composition for preventing or inhibiting hyperlipidemia comprising, as an active ingredient, an IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein.

Hereinafter, the present invention will be described in more detail.

The first, second and third aspects of the present invention provide the composition for inhibiting absorption of cholesterol, the composition for preventing or inhibiting obesity and the composition for preventing or inhibiting hyperlipidemia. All three aspects comprise, as an active ingredient, an IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein.

As can be seen from the following tests of the present invention, the IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein effectively inhibits absorption of cholesterol in the intestine (see FIG. 1 for inhibition mechanism).

Based on the aforementioned effects of absorption inhibition of cholesterol, the IgY-type antibody against an antigen that comprises, as an epitope, the entirety or part of amino acid sequences in the loop part that protrudes towards the lumen among NPC1L1 (Niemann-Pick C1-Like1) that is an intestinal cholesterol transport protein can be prepared and used as a composition for inhibiting absorption of cholesterol and a composition for preventing or inhibiting obesity and hyperlipidemia that result from overtake of cholesterol.

Meanwhile, NPC1L1 (Niemann-Pick C1-Like1) protein used in the present invention is a cholesterol transport protein present in the intestine. For example, human contains a nucleic acid sequence represented by sequence number 1 and an amino acid sequence represented by a sequence number 2. NPC1L1 is known to have an important role in absorption of cholesterol in small intestine. The absorption of cholesterol by NPC1L1 protein through endocytic recycling contributes to unidirectional (in vivo) absorption and is not affected by HDL, intracellular cholesterol absorption and concentration in blood. Also, NPC1L1 is known to selectively recognize non-esterified free cholesterol and thus facilitate unidirectional transport into hepatoma cells (J. Mark Brown at. al., Biochem. J. (2007) 406, 273-283).

In the present invention, an antibody to block the action of NPC1L1 described above is prepared, and in particular, an IgY-type antibody against an antigen that comprises, as an epitope, the entirety or part of amino acid sequences in the loop part that protrudes towards the lumen among NPC1L1 (Niemann-Pick C1-Like1) is produced and used. Since the sequence of the loop part that protrudes towards the lumen among NPC1L1 (Niemann-Pick C1-Like1) is known, the loop part is produced into peptide through biosynthesis or genetic recombination and may be used as an epitope.

Meanwhile, IgY is an antibody contained in yolk and an antibody developed into an IgY-type is known to have almost no side effects when ingested in the human body. IgY may be produced by injecting an antigen into a chicken. This method is known in the art and a detailed explanation thereof is thus omitted.

Meanwhile, the term "active ingredient" used herein means that the inhibitory effect of absorption of cholesterol in the composition and inhibitory effect of hyperlipidemia or obesity are derived from "IgY-type antibody" provided in the present invention, and means that a variety of aid ingredients other than these ingredients may be added in order to facilitate preservability and absorption.

Meanwhile, the loops that protrude towards the lumen among NPC1L1 (Niemann-Pick C1-Like1) are seven in total, have amino acid sequences represented by sequence numbers 4, 6, 8, 10, 12, 14 and 16, and are used as epitopes for production of antibodies. Accordingly, the amino acid sequence present in the loop part that protrudes towards the lumen among NPC1L1 that can be used as epitopes in the present invention is one of amino acid sequences represented by sequence numbers 4, 6, 8, 10, 12, 14 and 16.

Meanwhile, in the present invention, the antigen used for production of IgY-type anti-body may be formed by binding a carrier protein that can induce antigenicity to the entirety or part of amino acid sequences in the loop part that protrudes towards the lumen among NPC1L1 (Niemann-Pick C1-Like1). As molecular weight increases, antigenicity can be improved. At this time, as the carrier protein that induces antigenicity, one selected from bovine serum albumin (BSA), keyhole limpet haemocyanine (KLH) and ovalbumin (OVA) may be used.

Adavantagous Effects

The IgY-type antibody derived from yolk to NPC1L1 (Niemann-Pick C1-Like1), contained, as an active ingredient, in the composition of the present invention is linked to NPC1L1 (Niemann-Pick C1-Like1) that is a cholesterol transport protein in the intestines, thus interfering with binding between cholesterol and the transport protein to completely block absorption of cholesterol in the body and thereby prevent hyperlipidemia and obesity.

BRIEF DESCRIPTION OF THE DRAWINGS

The above and other objects, features and other advantages of the present invention will be more clearly understood from the following detailed description taken in conjunction with the accompanying drawings, in which:

In FIG. 9, 'COM' and 'ISA' mean the kinds of adjuvant and ISA means an anti-NPC1L1 IgY sample produced using 'ISA 70 adjuvant', and 'COM' means an anti-NPC1L1 IgY sample produced using a 'Complete Freund adjuvant (Difco, USA)'.

BEST MODE

Figure 1:
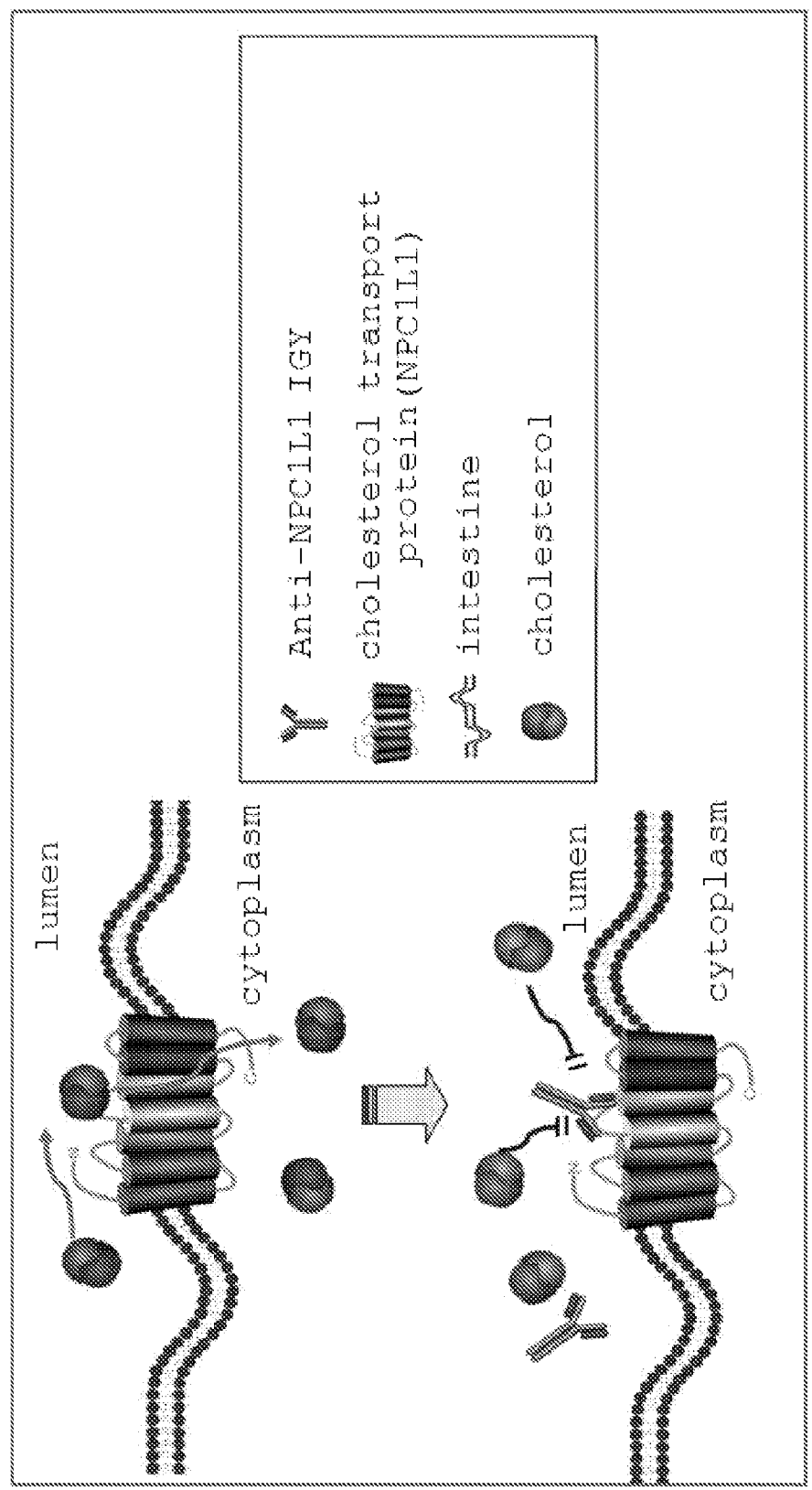
FIG. 1 is a schematic view illustrating a mechanism in which an anti-NPC1L1 IgY inhibits absorption of cholesterol.

Hereinafter, the following examples will be provided for a further understanding of the invention. The scope of the present invention is not limited to the following examples and includes technical spirits equivalent thereto.

PRODUCTION EXAMPLE 1

Production of Recombinant Antigen and Confirmation of Suitability

Hereinafter, a recombinant antigen (hereinafter, referred to as 'protein 373') was produced by cloning a total of 262 amino acids represented by amino acid sequence numbers 373 to 634 so that the recombinant antigen has amino acid of loop 1 (the second loop, among a total of seven loops that NPC1L1 have in a lumen direction) represented by sequence number 4, among the overall amino acid sequence of NPC1L1.

Also, a recombinant antigen (hereinafter, referred to as 'protein 416') was produced by cloning a total of 220 amino acids represented by amino acid sequence numbers 416 to 635 among the overall amino acid sequence of NPC1L1.

Also, a recombinant antigen (hereinafter, referred to as 'protein 509') was produced by cloning a total of 125 amino acids represented by amino acid sequence numbers 509 to 633 among the overall amino acid sequence of NPC1L1.

The respective cloned DNA sequences used for production of antigens to produce IgY were ligated into the Xho I/BamH I cloning site of pET-15b vector having a His-tag for purification and then expressed in an $E.\ coli$ BL21 (DE3) host using IPTG.

After over-expression, the DNA sequences were purified on a His6 affinity column and solubilized, and the resulting recombinant protein was subjected to SDS-PAGE and western blotting.

The antibodies used for western blotting herein were commercially available anti-NPC1L1 mouse monoclonal antibodies and HRP-conjugated anti-mouse goat antibodies.

Figure 2:
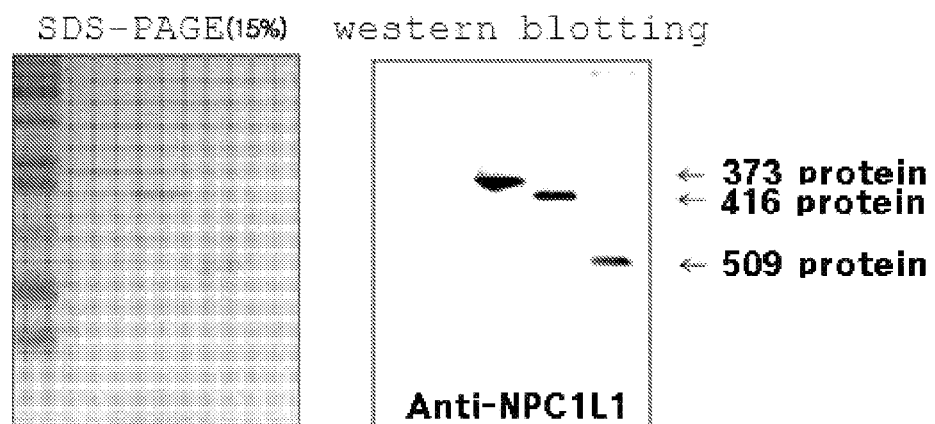
FIG. 2 illustrates test results of production of recombinant antigen that produces IgY and antigenicity of the produced antigen.

The test results are shown in FIG. 2. From the fact that the over-expressed and purified recombinant NPC1L1 antigens (proteins 373, 416 and 509) reacted with anti-NPC1L1 antibodies derived from the mouse, it could be seen that the NPC1L1 antigens were produced as recombinant proteins having a main epitope and had an antibody property of producing IgY that inhibits the function of NPC1L1 protein.

EXAMPLE

Production of IgY Antibody Through Vaccine of Recombinant Antigen (1) Preparation of vaccine A vaccine was prepared by mixing the recombinant peptide-type antibody-type NPC1L1 antigen produced in Production Example 1 above and Freund's complete adjuvant (Difco 263810, USA) at equivalent volumes. In order to confirm difference in formation of antibodies depending on presence of adjuvant, ISA70 (general adjuvant) and an antigen were mixed at equivalent amounts using a syringe to prepare a vaccine for production of specific-yolk antibody.

The conjugation between the recombinant peptide and the carrier was performed using meleimide-activated BSA and KLH conjugated kit (Maleimide Activated BSA, KLH conjugation Kit, Sigma-Aldrich, MBK1, USA) and this method was performed in accordance with the instruction manual. The method will be described in brief. A carrier protein was dissolved in pH 6.6 in 20 mM sodium phosphate, 230 mM NaCl, 2 mM EDTA, and 80 mM sucrose, recombinant peptide was dissolved in pH 6.6 in 20 mM sodium phosphate, 100 mM EDTA and 80 mM EDTA, the carrier protein and the recombinant peptide were mixed and stirred in a refrigeration for 12 hours or longer, and finally separated on a Sepadex G-25M gel filtration column.

(2) Immunization of Egg-Laying Chickens

The prepared vaccine was intramuscularally injected into 22-week old Hy-line brown egg-laying chickens, was primarily inoculated at an interval of three weeks and was boosted twice.

(3) Separation and Confirmation of Immune-Yolk Antibody i) Separation of Immune-Yolk Antibody IgY was isolated from eggs produced from the immunized egg-laying chicken using ammonium sulfate (sigma USA). The ammonium sulfate method was carried out by removing an egg membrane from yolk, diluting with pH 2.5 D.W at a ratio of 1:4, freezing the dilute at −20° C. for 2 days, centrifuging the dilute at 7000 rpm for 30 minutes, and filtering the supernatant to separate a water soluble protein in accordance with the method of Akita et., Al. (Akita, E. M. and Nakai, S. Immunoglobulins from egg yolk: isolation and purification. J. Food. Sci., 57: 629-633, 1992). A pure protein was precipitated from the separated protein with an over-saturated ammonium sulfate solution at 4° C. overnight. The precipitated solution was centrifuged to obtain a pellet, re-suspended with PBS, and dialyzed at 4° C. with a PBS buffer to harvest the separated antibody sample.

ii) Electrophoresis

Figure 3:
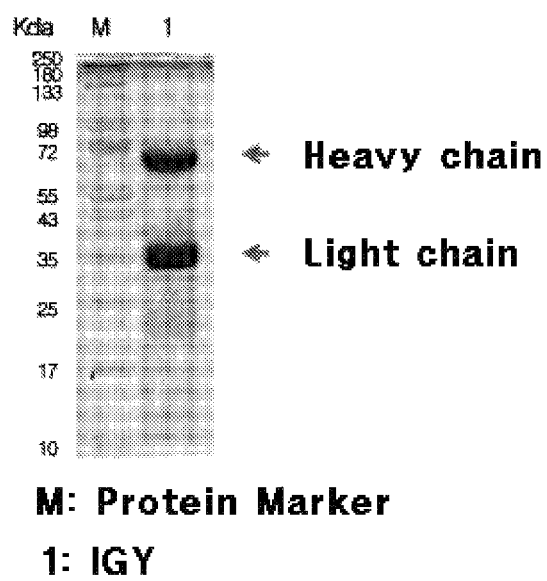
FIG. 3 illustrates electrophoresis results of the produced recombinant an antibody, IgY.

Sodium dodecyl sulfate-polyacrylamide gel electrophoresis (SDS-PAGE) was performed using 5% stacking gel and 10% seperating gel) in accordance with the method of Laemmli (Laemmli. U.K. Cleavage of structural proteins during the assembly of the head of bacteriophage T4. Nature, 227 (5259): 680-685, 1970). After electrophoresis, the gel was stained with a Coomassie brilliant blue R-250 solution for 30 minutes and the separated IgY antibody was confirmed using a destaining buffer. FIG. 3 shows electrophoresis results of the produced recombinant antibody, IgY.

(4) Confirmation of Binding of Separated IgY to Antigen

Figure 4:
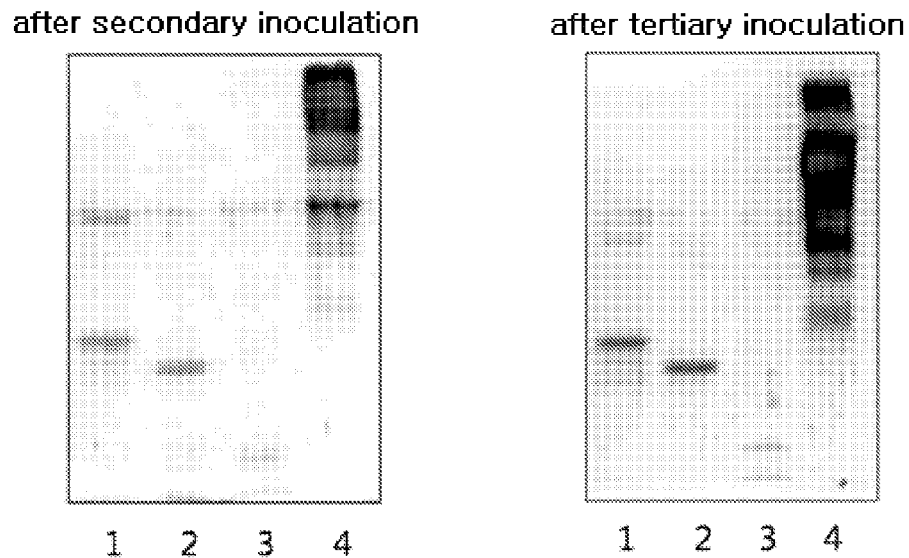
FIG. 4 illustrates western blot results of the binding capability of a recombinant antibody, IgY to antigen.

The binding between the separated IgY antibody and peptide antigen was confirmed by western blotting. As a result, as shown in FIG. 4, it was confirmed that IgY produced by immunization recognized recombinant protein that contained the C loop part of NPC1L1 and was conjugated.

Test Example 1

Confirmation of Formation of Antibody Using ELISA Test Method

In this Test Example, whether or not an antibody was formed by the vaccine (protein 416) prepared using the complete adjuvant and the ISA 70 adjuvant was confirmed in accordance with an ELISA test method.

a) The NPC1L1-BSA-conjugated antigen was coated at a concentration of 400 ng/ml on a 96-well ELISA plate using a carbonate buffer and incubated at 37° C. for one hour to complete coating.

b) The antigen was washed with PBST three times and blocked with 1%-BSA at 37° C. for one hour.

c) The antigen was washed with PBST three times, was treated with 100 ul of a sample and incubated at 37□ for one hour.

d) The antigen was washed with PBST three times, treated with 100 ul of anti-chicken-IgY-HRP as a secondary antibody and incubated at 37° C. for one hour.

e) The antigen was washed with PBST three times, 100 ul of a prepared substrate solution was added thereto, and color reaction was performed for 10 minutes and was ceased with 2N sulfuric acid.

f) The results were confirmed using an ELISA reader.

Figure 5:
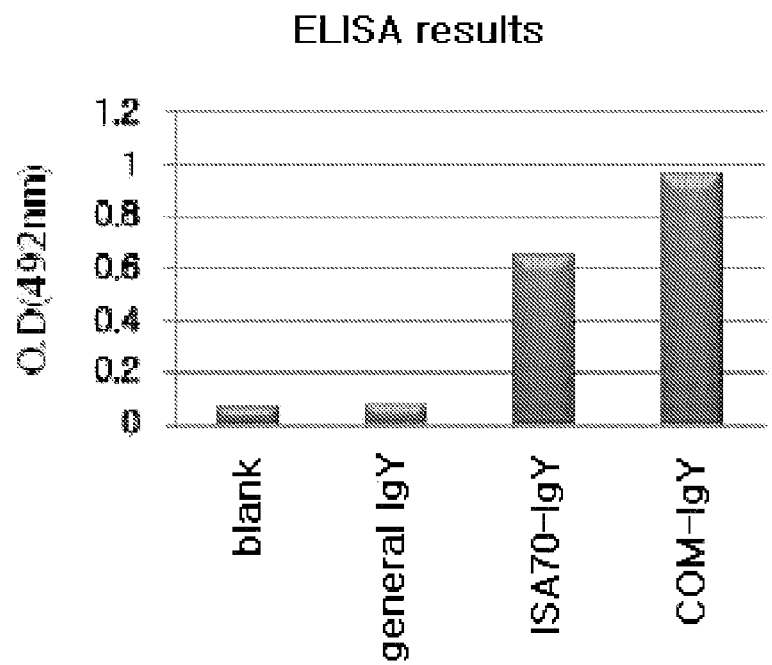
FIG. 5 illustrates ELISA results quantitatively showing whether or not vaccine forms an antibody, IgY.

In accordance with the test results (FIG. 5) and the results of antibody samples diluted at a ratio of 1:10,000, when comparing the blank value with ISA70-IgY, and COM-IgY, the difference in O.D of about 10- to 15-fold was observed.

There was no difference in O.D between the sample of the general IgY and the blank. This means that an anti-NPC1L1-IgY antibody was formed.

Also, regarding formation of antibody caused by the difference between adjuvants, the Freund's complete adjuvant (Difco 263810, USA) containing OMP of microorganisms exhibited superior titer, as compared to the ISA 70 adjuvant.

From results of western blotting test of Example 1 and the present ELISA test, it could be seen that the anti-NPC1L1-IgY antibody was well formed and an antibody was bound to the antigen.

Test Example 2

Immunofluorescence of In Vitro NPC1L1

In order to confirm whether the anti-NPC1L1 IgY antibody (antibody to protein 416) separated from yolk was bound to an NPC1L1 protein as an antigen, hepatoma cell lines, HepG2 cell lines that are known to over-express NPC1L1 were subjected to in vitro immunofluorescence. (Davies J P, Scott C, Oishi K, Liapis A, Ioannou Y A. Inactivation of NPC1L1 causes multiple lipid transport defects and protects against diet-induced hypercholesterolemia. J Biol. Chem. 2005 Apr. 1; 280(13):12710-20. Epub 2005 Jan. 25.)

The cells were seeded at a concentration of $1 \times 10^4$/ml on a slide chamber, incubated for 18 hours and then tested. The cell medium was removed, the cells were fixed with 3.7% formaldehyde, washed with PBST, treated with a permeabilization buffer (0.2% Triton X-100) for 20 minutes, each of 2.5 ug/ml of anti-NPC1L1-IgY as a primary antibody and rabbit-anti-NPC1L1 (Santa Cruz, USA) as a commercial antibody was diluted at a ratio of 1/50 and the cells were treated with each diluted antibody. The cells were washed with PBS, each of anti-chicken IgY-Alexa488 (Biotium, USA) as a secondary antibody and anti-rabbit IgG-Alexa488 (Invitrogen, USA) was diluted at a ratio of 1/100, the cells were treated with each diluted antibody at room temperature (RT) for one hour and washed with PBS, the nucleus was counterstained with Hoechst33258 for 30 minutes and mounted, and the results were observed using a multi-photon confocal laser scanning microscope (LSM 510 META NLO, Carl Zeiss, Germany).

Figure 6:
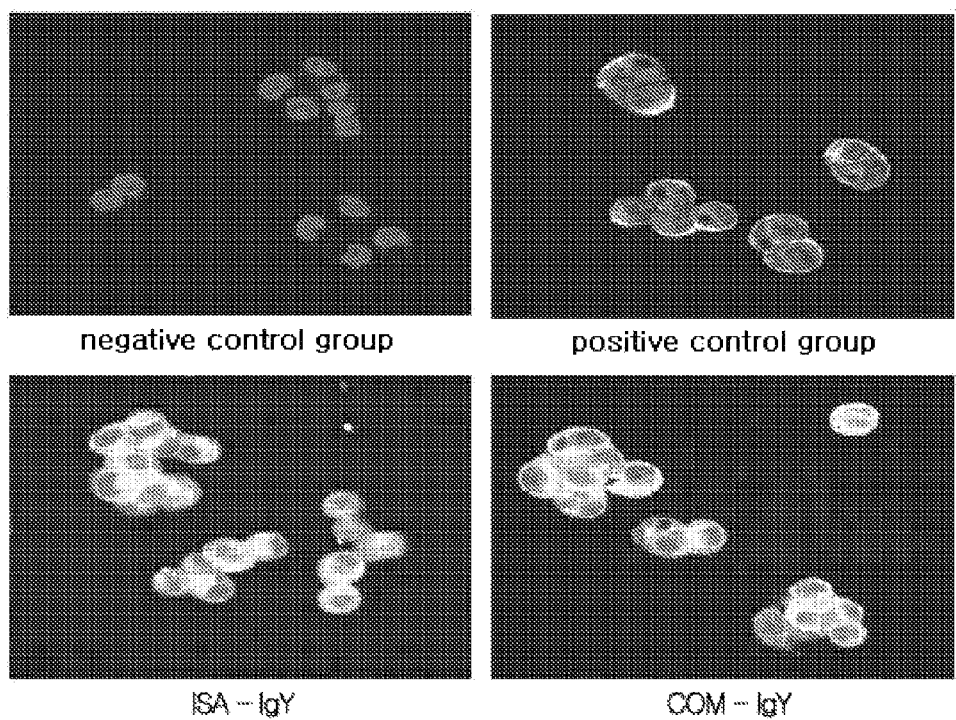
FIG. 6 illustrates in vitro immunofluorescence results confirming binding of IgY to NPC1L1 protein using HepG2 cell lines. The results are obtained by observation at a magnification of 400× using a confocal microscope.

As could be seen from the results of immunofluorescence (IF) (FIG. 6), except that a negative control that was not treated with a primary antibody, the anti-NPC1L1 IgY antibody was bound to NPC1L1 as an antigen and expressed in cytoplasm, and the antibody produced from yolk was well bound to the target protein.

Test Example 3

In Vivo Immunohistochemistry and Immunofluorescence

It could be seen from the results that the anti-NPC1L1-IgY (antibody to protein 416) was in vitro bound to the NPC1L1 protein and, immunohistochemistry (IHC) and immunofluorescence (IF) were performed using mouse intestine tissues in order to confirm whether or not the anti-NPC1L1-IgY was bound to the NPC1L1 protein actually present in small intestines.

(1) In Vivo Immunohistochemistry

In order to confirm whether or not the anti-NPC1L1-IgY separated from yolk was bound to the NPC1L1 protein, immunohistochemistry was performed on the mouse intestine tissues.

Altmann et., al. (Altmann S W, Davis H R Jr, Zhu L J, Yao X, Hoos L M, Tetzloff G, Iyer S P, Maguire M, Golovko A, Zeng M, Wang L, Murgolo N, Graziano M P. Niemann-Pick C1 Like 1 protein is critical for intestinal cholesterol absorption. Science. 2004 Feb. 20; 303(5661):1201-4) reported that a great amount of small intestinal NPC1L1s was distributed in the small intestine proximal part.

Accordingly, the mouse small intestine was harvested, the jejunum of the proximal part except the duodenum was separated and washed with PBS to remove foods present in the intestinal canal, fixed with 4% paraformaldehyde, fixed with paraffin using an automatic tissue processor (Leica, Germany), embedded (Leica, Germany) to produce a paraffin block, and cut to a size of 5 μm with a tissue microtome (Leica, Germany) to produce a slide sample for immunostaining.

The slide was deparaffinized with xylene, hydrated in ethanol series (100%, 95%, 90%, 80%, 70%, 50%), washed with PBS, treated with 0.3% $H_2O_2$ to remove endogenous peroxidase, blocked with 5% normal serum (Vector, USA), treated with a predetermined concentration of anti-NPC1L1-IgY (2.5 ug/ml) separated from yolk and a commercial antibody (rabbit-anti-NPC1L1, 1/50, Santa Cruz, USA) as primary antibodies, and incubated at 4° C. overnight. The sample was washed with PBS, treated with a diluted (1/100) secondary antibody (Anti-Chicken Biotin, Anti-Rabbit-Biotin, Vetor, USA) at room temperature (RT) for 2 hours, washed with PBS, and ABC was incubated using a VECTASTAIN ABC Kit (Vetor, USA) for 2 hours. The ABC was reacted with a DAB solution (Vetor, USA) for 2 to 5 minutes, washed with PBS, counter-stained with hematoxylin (Vector, USA), washed with D.W, dehydrated with ethanol series, treated with xylene and mounted, and the results were observed using an optical microscope (Carl Zeiss, Germany).

(2) In Vivo Immunofluorescence

In order to confirm whether or not the anti-NPC1L1-IgY separated from yolk was bound to the NPC1L1 protein, immunofluorescence was performed on the mouse intestine tissues. The tissue paraffin xylene was deparaffinized with xylene, hydrated in ethanol series (100%, 95%, 90%, 80%, 70%, 50%), washed with PBS, treated with 0.3% $H_2O_2$ to remove endogenous peroxidase, blocked with 5% normal serum (Vector, USA), treated with a predetermined concentration of anti-NPC1L1-IgY (2.5 ug/ml) separated from yolk and a commercial antibody (rabbit-anti-NPC1L1, 1/50, Santa Cruz, USA) as primary antibodies, and incubated at 4° C. overnight. The sample was washed with PBS, treated with each 1/100 dilution of anti-chicken IgY-Alexa488 (Biotium, USA) and anti-rabbit IgG-Alexa488 (Invitrogen, USA) as secondary antibodies at room temperature for 2 hours, washed with PBS, nucleus was counterstained with Hoechst33258 and mounted, and the results were observed with an optical microscope (Carl Zeiss, Germany).

(3) Test Results

Figure 7:
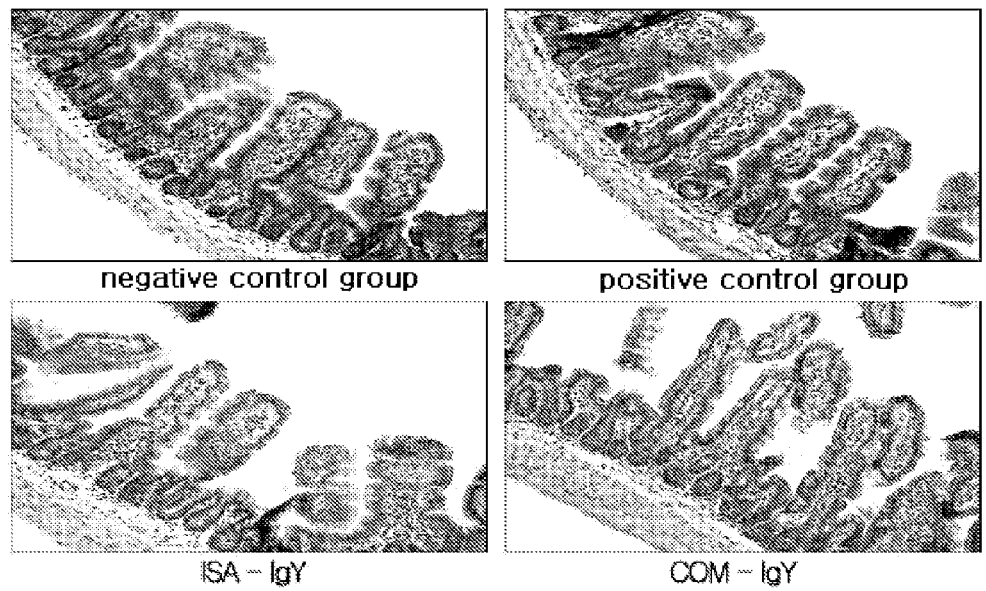
FIG. 7 illustrates in vivo immunohistochemistry results confirming bonding of IgY to a NPC1L1 protein in the mouse small intestine tissue. The results are obtained by observation at a magnification of 200× using a confocal microscope.
Figure 8:
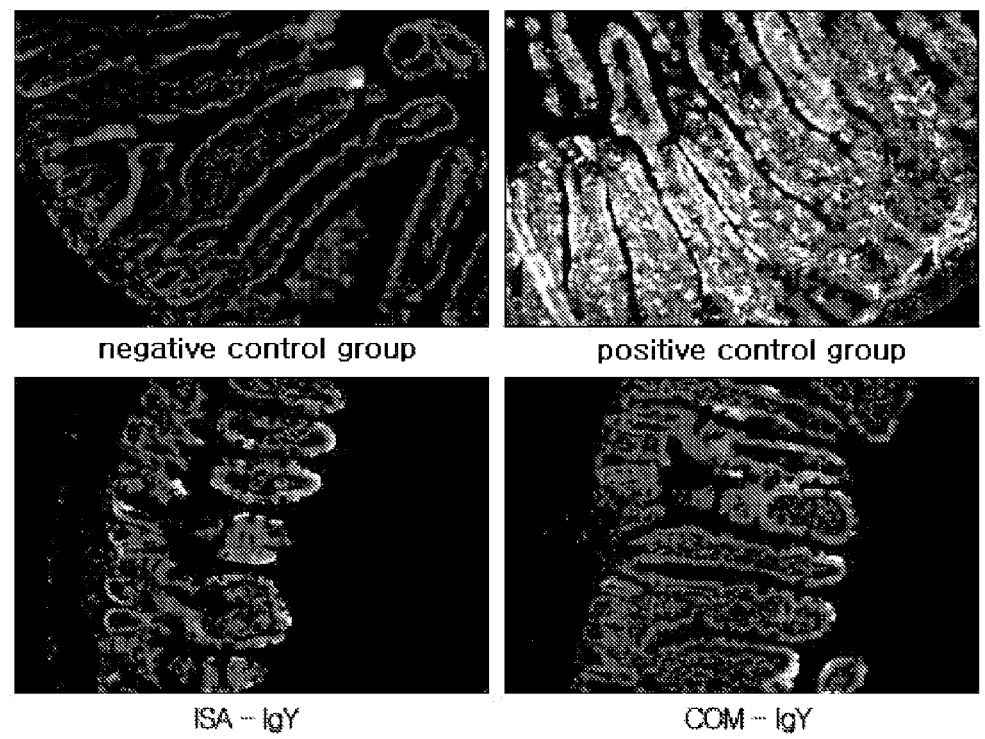
FIG. 8 illustrates in vivo immunofluorescence results confirming binding of IgY to a NPC1L1 protein in mouse small intestine tissues. The results are obtained by observation at a magnification of 200× using a confocal microscope.

As can be seen from the results shown in FIGS. 7 and 8, the anti-NPC1L1 IgY antibody was strongly expressed throughout the ileal villus distal part and was expressed in the proximal part other than the villus distal part, and, it was confirmed through IF that fluorescence was strongly emitted in the form of a line in epithelial cells of the villus distal part.

It could be seen from these results that IgY produced in the present invention was actually bound even in small intestines.

Test Example 4

Cholesterol Uptake Assay of Anti-NPC1L1 IgY antibody

In order to confirm efficacies and effects of anti-NPC1L1 IgY (antibody to protein 416) cholesterol uptake assay was performed using Hep G2 cells.

Hep G2 cells were incubated at a density of $2\times10^5$/ml on a 24-well plate using a DMEM (Difco, USA) medium containing 10% FBS (Difco, USA) for 18 hours, treated with anti-NPC1L1 IgY at different concentrations (5, 25 and 50 ug/ml), and treated with 10 ug/ml of Ezetimibe known as a cholesterol uptake inhibitor as a positive control. Each sample was pre-incubated at 37° C. for one hour and then was removed, and a fresh medium was added thereto, followed by washing. The sample was treated with 50 uM of radio isotope-labeled [3H]-cholesterol for 3 hours. The cells were washed with 0.1% fatty acid-free BAS-containing PBS, collected with HESS (Difco, USA), cytolysis was performed with 1% Triton X-100 (Sigma, USA)-containing HESS, radiation dose was measured with a Beckmen LS6500 scintillation counter, and comparison and assay were performed using a group to which IgY was administered as a control group.

Figure 9:
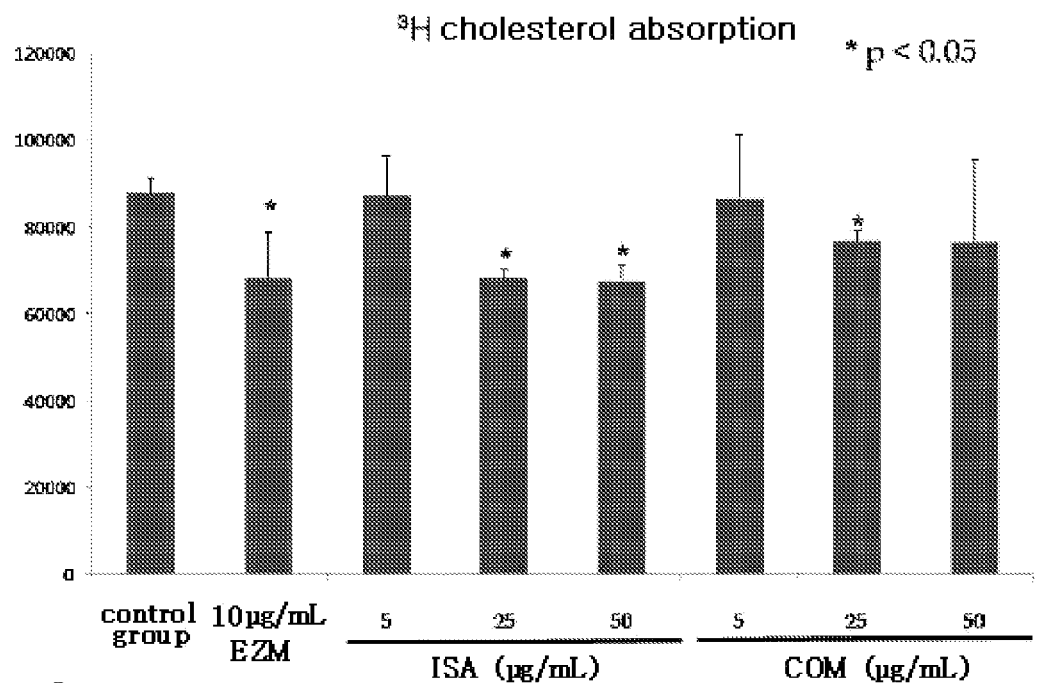
FIG. 9 illustrates cholesterol uptake inhibition test results using HepG2 cell lines.

As can be seen from the result of FIG. 9, as compared to the non-treated control group, Ezetimibe serving as a positive control exhibited a significant decrease ($p<0.05$) at a concentration of 10 ug/ml, and IgY exhibited a significant decrease ($p<0.05$) in cholesterol uptake at a concentration of 25 ug/ml. In FIG. 9, 'COM' and 'ISA' represent the types of adjuvant, "ISA" means an anti-NPC1L1 IgY treatment group using 'ISA 70 adjuvant', and 'COM' means an anti-NPC1L1 IgY treatment group using a 'Complete Freund adjuvant (Difco, USA)'.

These results indicate that the produced anti-NPC1L1 IgY antibody is effectively bound to the NPC1L1 protein, and the bound IgY significantly inhibits cholesterol uptake of NPC1L1. That is, the anti-NPC1L1 IgY of the present invention is an antibody that has the same effects as Ezetimibe, the drug, known to be a conventional cholesterol uptake inhibitor.

Test Example 5

Animal Test of Anti-NPC1L1 Igy Antibody

An animal test was performed in order to confirm efficacies of anti-NPC1L1 IgY antibody (antibody to protein 416) bound to NPC1L1 (Niemann-Pick C1 Like1), intestinal cholesterol transport protein.

(1) Test Animal

The test animals used herein were 5-week old C57BL/6 female mice available from KOATECH (Korea) and the animals were acclimatized for 7 days, animals were classified into groups (n=10) the day before of the test, and grouping was performed in a state that the average weight of all test groups was identical. The test animals were grown in a polycarbonate cage (width 26 cm, length 42 cm, height 18 cm), and were bred while they were fed with sterilized distilled water and feed with experimental animal (Purina Korea, Inc.), all groups except the normal group were freely fed with an atherogenic diet (available from Central Lab. Animal Inc. D12336, Research diets, INC. USA) so that they digested a high concentration of cholesterol during the test term. The test animals were tested in accordance with the instructions of test animal ethics commission in Chuncheon bioindustry foundation.

(2) Administration of Test Group and Test Material

The average weight of all test groups was made identical and test groups were classified. The animals were classified into five groups in total, and were roughly divided into a normal group that was not treated and a group to which a high cholesterol feed was administered, a control group for high cholesterol feed, and an IgY control group and an IgY administration group that were classified depending on the administration of IgY. IgY was administered in amounts of 50 mg and 250 mg per animal weight kg, anti-*helicobacter pylori* IgY was administered in an amount of 250 mg per animal weight kg to an IgY control group, and PBS was administered to the normal group and the control group.

(3) Measurement of Body Weight

The test animals were labeled on the ear thereof using an ear punch for animals in accordance with an individual identification method, and a weight increase percentage was measured with respect to 100% of the test initial weight. The weight was measured at a predetermined time once a week.

(4) Statistical Treatment

The significance of the test results was identified by a one way ANOVA-test using a GraphPad 4.0 prism program and was expressed with respect to the control group to which the high cholesterol feed was administered.

(5) Test Results

Figure 10:
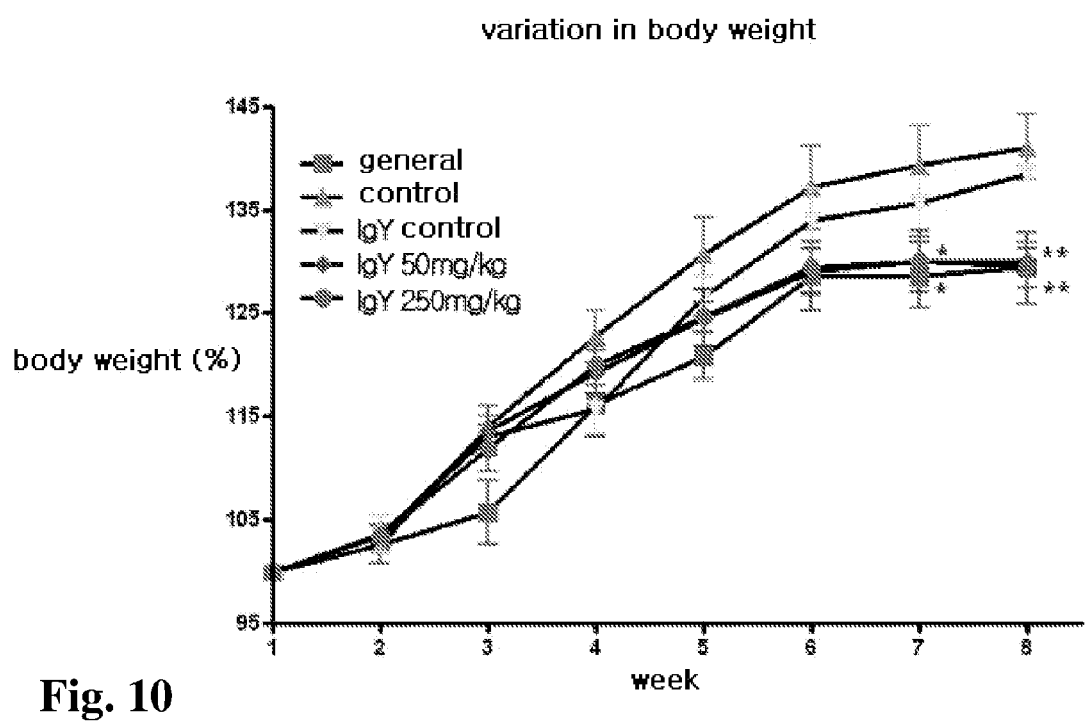
FIG. 10 illustrates variation in body weight while a high cholesterol feed was ingested over 8 weeks (*; $p<0.05$, **; $p<0.01$).

As can be seen from FIG. 10, as a result of administration of high cholesterol feed, the weight increase percentage was rapidly elevated at three weeks after the test, and a weight increase percentage showing a broad curve was observed after 6 weeks, and assuming that the test initial weight was 100%, the control group to which a high cholesterol feed was administered exhibited a 41% increase in weight, while the group to which the anti-NPC1L1-IgY was administered exhibited 30% and 29% increase percentages in weight, which means that the increase percentage in body weight caused by the feed was significantly decreased ($p<0.01$).

Also, in order to confirm the effects of administration of IgY, the group to which the anti-America *helicobacter pylori* IgY was administered did not exhibit the inhibitory effect of administered IgY on the body weight increase.

Accordingly, it may be thought that IgY effectively acts on intestinal cholesterol transport protein, NPC1L1, thus significantly inhibiting a weight increase.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

[Sequence Free Text]

Seq. No. 1 represents a nucleic acid sequence that encodes NPC1L1 (Niemann-Pick C1 Like 1), cholesterol transport proteins present in the intestines of the human.

Seq. No. 2 represents an amino acid sequence that encodes NPC1L1 (Niemann-Pick C1 Like 1), cholesterol transport proteins present in the intestines of the human.

Seq. Nos. 4, 6, 8, 10, 12, 14 and 16 represent amino acid sequences of seven loops that protrude towards the lumen among NPC1L1 (Niemann-Pick C1-Like 1).

Seq. Nos. 3, 5, 7, 9, 11, 13 and 15 represent nucleic acid sequences that encode Seq. Nos. 4, 6, 8, 10, 12, 14 and 16 amino acid sequences, respectively.

The invention claimed is:

1. A food composition for treating obesity comprising, as an active ingredient, an IgY-type antibody against an antigen that comprises, as an epitope, amino acid sequence numbers 416 to 635 of NPC1L1 (Niemann-Pick C1-Like1) that is an intestinal cholesterol transport protein encoded by the amino acid sequence of SEQ. ID. No:2.

2. A food composition for treating hyperlipidemia comprising, as an active ingredient, an IgY-type antibody against an antigen that comprises, as an epitope, amino acid sequence numbers 416 to 635 of NPC1L1 (Niemann-Pick C1-Like1) that is an intestinal cholesterol transport protein encoded by the amino acid sequence of SEQ. ID. No:2.

* * * * *

SEQUENCE LISTING

<160> NUMBER OF SEQ ID NOS: 16

<210> SEQ ID NO 1
<211> LENGTH: 3996
<212> TYPE: DNA
<213> ORGANISM: Homo sapiens
<220> FEATURE:
<221> NAME/KEY: gene
<222> LOCATION: (1)..(3996)
<223> OTHER INFORMATION: NPC1L1

<400> SEQUENCE: 1

| | | | | | | |
|---|---|---|---|---|---|---|
| atggcggagg | ccggcctgag | gggctggctg | ctgtgggccc | tgctcctgcg | cttggcccag | 60 |
| agtgagcctt | acacaaccat | ccaccagcct | ggctactgcg | ccttctatga | cgaatgtggg | 120 |
| aagaacccag | agctgtctgg | aagcctcatg | acactctcca | acgtgtcctg | cctgtccaac | 180 |
| acgccggccc | gcaagatcac | aggtgatcac | ctgatcctat | acagaagat | ctgccccgc | 240 |
| ctctacaccg | gccccaacac | ccaagcctgc | tgctccgcca | agcagctggt | atcactggaa | 300 |
| gcgagtctgt | cgatcaccaa | ggccctcctc | acccgctgcc | cagcctgctc | tgacaatttt | 360 |
| gtgaacctgc | actgccacaa | cacgtgcagc | cccaatcaga | gcctcttcat | caatgtgacc | 420 |
| cgcgtggccc | agctaggggc | tggacaactc | ccagctgtgg | tggcctatga | ggccttctac | 480 |
| cagcatagct | ttgccgagca | gagctatgac | tcctgcagcc | gtgtgcgcgt | ccctgcagct | 540 |
| gccacgctgg | ctgtgggcac | catgtgtggc | gtgtatggct | ctgcccttttg | caatgcccag | 600 |
| cgctggctca | acttccaggg | agacacaggc | aatggtctgg | ccccactgga | catcaccttc | 660 |
| cacctcttgg | agcctggcca | ggccgtgggg | agtgggattc | agcctctgaa | tgaggggggtt | 720 |
| gcacgttgca | atgagtccca | aggtgacgac | gtggcgacct | gctcctgcca | agactgtgct | 780 |
| gcatcctgtc | ctgccatagc | ccgccccag | gccctcgact | ccaccttcta | cctgggccag | 840 |
| atgccgggca | gtctggtcct | catcatcatc | ctctgctctg | tcttcgctgt | ggtcaccatc | 900 |
| ctgcttgtgg | gattccgtgt | ggcccccgcc | agggacaaaa | gcaagatggt | ggaccccaag | 960 |
| aagggcacca | gcctctctga | caagctcagc | ttctcccacc | cacccctcct | tggccagttc | 1020 |
| ttccagggct | ggggcacgtg | ggtggcttcg | tggcctctga | ccatcttggt | gctatctgtc | 1080 |
| atcccggtgg | tggccttggc | agcgggcctg | gtctttacag | aactcactac | ggaccccgtg | 1140 |
| gagctgtggt | cggccccccaa | cagccaagcc | cggagtgaga | agctttccca | tgaccagcat | 1200 |
| ttcggcccct | cttccgaac | caaccaggtg | atcctgacgg | ctcctaaccg | gtccagctac | 1260 |
| aggtatgact | ctctgctgct | ggggcccaag | aacttcagcg | gaatcctgga | cctggacttg | 1320 |
| ctgctggagc | tgctagagct | gcaggagagg | ctgcggcacc | tccaggtatg | gtcgcccgaa | 1380 |
| gcacagcgca | acatctccct | gcaggacatc | tgctacgccc | cctcaatcc | ggacaatacc | 1440 |
| agtctctacg | actgctgcat | caacagcctc | tgcagtatt | tccagaacaa | ccgcacgctc | 1500 |
| ctgctgctca | cagccaacca | gacactgatg | gggcagacct | cccaagtcga | ctggaaggac | 1560 |
| cattttctgt | actgtgccaa | tgccccgctc | accttcaagg | atggcacagc | cctggcctg | 1620 |
| agctgcatgg | ctgactacgg | ggcccctgtc | ttcccttcc | ttgccattgg | ggggtacaaa | 1680 |
| ggaaaggact | attctgaggc | agaggccctg | atcatgacgt | tctcccctcaa | caattaccct | 1740 |
| gccggggacc | ccgtctgggc | ccaggccaag | ctgtgggagg | aggccttctt | agaggaaatg | 1800 |
| cgagccttcc | agcgtcggat | ggctggcatg | ttccaggtca | cgttcatggc | tgagcgctct | 1860 |
| ctggaagacg | agatcaatcg | caccacagct | gaagacctgc | ccatctttgc | caccagctac | 1920 |

-continued

```
attgtcatat tcctgtacat ctctctggcc ctgggcagct attccagctg gagccgagtg    1980
atggtggact ccaaggccac gctgggcctc ggcggggtgg ccgtggtcct gggagcagtc    2040
atggctgcca tgggcttctt ctcctacttg ggtatccgct cctccctggt catcctgcaa    2100
gtggttcctt tcctggtgct gtccgtgggg gctgataaca tcttcatctt tgttctcgag    2160
taccagaggc tgccccggag gcctgggggag ccacgagagg tccacattgg gcgagccta    2220 ggcagggtgg ctcccagcat gctgttgtgc agcctctctg aggccatctg cttcttccta    2280
ggggccctga ccccatgcc agctgtgcgg acctttgccc tgacctctgg ccttgcagtg    2340
atccttgact tcctcctgca gatgtcagcc tttgtggccc tgctctccct ggacagcaag    2400
aggcaggagg cctcccggtt ggacgtctgc tgctgtgtca agcccaggaa gctgcccccg    2460
cctggccagg gagaggggct cctgcttggc ttcttccaaa aggcttatgc cccctcctg     2520 ctgcactgga tcactcgagg tgttgtgctg ctgctgtttc tcgccctgtt cggagtgagc    2580
ctctactcca tgtgccacat cagcgtggga ctggaccagg agctggccct gcccaaggac    2640
tcgtacctgc ttgactattt cctctttctg aaccgctact tcgaggtggg ggccccggtg    2700
tactttgtta ccaccttggg ctacaacttc tccagcgagg ctgggatgaa tgccatctgc    2760
tccagtgcag gctgcaacaa cttctccttc acccagaaga tccagtatgc cacagagttc    2820
cctgagcagt cttacctggc catccctgcc tcctcctggg tggatgactt cattgactgg    2880
ctgaccccgt cctcctgctg ccgcctttat atatctggcc caataagga caagttctgc     2940 ccctcgaccg tcaactctct gaactgccta aagaactgca tgagcatcac gatgggctct    3000
gtgaggccct cggtggagca gttccataag tatcttcctt ggttcctgaa cgaccggccc    3060
aacatcaaat gtcccaaagg cggcctggca gcatacagca cctctgtgaa cttgacttca    3120
gatggccagg ttttagcctc caggttcatg gcctatcaca agcccctgaa aaactcacag    3180
gattacacag aagctctgcg ggcagctcga gagctggcag ccaacatcac tgctgacctg    3240
cggaaagtgc ctggaacaga cccggcttt gaggtcttcc cctacacgat caccaatgtg    3300 tttatgagc agtacctgac catcctcct gagggggctct tcatgctcag cctctgcctt    3360
gtgcccacct tcgctgtctc ctgcctcctg ctgggcctgg acctgcgctc cggcctcctc    3420
aacctgctct ccattgtcat gatcctcgtg gacactgtcg gcttcatggc cctgtggggc    3480
atcagttaca atgctgtgtc cctcatcaac ctggtctcgg cggtgggcat gtctgtggag    3540
tttgtgtccc acattacccg ctcctttgcc atcagcacca agcccacctg gctggagagg    3600
gccaaagagg ccaccatctc tatgggaagt gcggtgtttg caggtgtggc catgaccaac    3660
ctgcctggca tccttgtcct gggcctcgcc aaggcccagc tcattcagat cttcttcttc    3720
cgcctcaacc tcctgatcac tctgctgggc ctgctgcatg gcttggtctt cctgcccgtc    3780
atcctcagct atgtggggcc tgacgtcaac ccggctctgg cactggagca gaagcgggct    3840
gaggaggcgc tggcagcagt catggtggcc tcttgcccaa atcaccctc ccgagtctcc     3900 acagctgaca acatctatgt caaccacagc tttgaaggtt ctatcaaagg tgctggtgcc    3960
atcagcaact tcttgcccaa caatgggcgg cagttc                               3996
```

<210> SEQ ID NO 2
<211> LENGTH: 1332
<212> TYPE: PRT
<213> ORGANISM: Homo sapiens

<400> SEQUENCE: 2

```
Met Ala Glu Ala Gly Leu Arg Gly Trp Leu Leu Trp Ala Leu Leu Leu
1               5                   10                  15
```

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
            35                  40                  45

Leu Met Thr Leu Ser Asn Val Ser Cys Leu Ser Asn Thr Pro Ala Arg
50                      55                  60

Lys Ile Thr Gly Asp His Leu Ile Leu Leu Gln Lys Ile Cys Pro Arg
65                      70                  75                  80

Leu Tyr Thr Gly Pro Asn Thr Gln Ala Cys Cys Ser Ala Lys Gln Leu
            85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
            115                 120                 125

Cys Ser Pro Asn Gln Ser Leu Phe Ile Asn Val Thr Arg Val Ala Gln
            130                 135                 140

Leu Gly Ala Gly Gln Leu Pro Ala Val Val Ala Tyr Glu Ala Phe Tyr
145                     150                 155                 160

Gln His Ser Phe Ala Glu Gln Ser Tyr Asp Ser Cys Ser Arg Val Arg
            165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
            195                 200                 205

Thr Gly Asn Gly Leu Ala Pro Leu Asp Ile Thr Phe His Leu Leu Glu
210                     215                 220

Pro Gly Gln Ala Val Gly Ser Gly Ile Gln Pro Leu Asn Glu Gly Val
225                     230                 235                 240

Ala Arg Cys Asn Glu Ser Gln Gly Asp Val Ala Thr Cys Ser Cys
            245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
            275                 280                 285

Ile Ile Leu Cys Ser Val Phe Ala Val Val Thr Ile Leu Leu Val Gly
            290                 295                 300

Phe Arg Val Ala Pro Ala Arg Asp Lys Ser Lys Met Val Asp Pro Lys
305                     310                 315                 320

Lys Gly Thr Ser Leu Ser Asp Lys Leu Ser Phe Ser Thr His Thr Leu
            325                 330                 335

Leu Gly Gln Phe Phe Gln Gly Trp Gly Thr Trp Val Ala Ser Trp Pro
            340                 345                 350

Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
            370                 375                 380

Ala Pro Asn Ser Gln Ala Arg Ser Glu Lys Ala Phe His Asp Gln His
385                     390                 395                 400

Phe Gly Pro Phe Phe Arg Thr Asn Gln Val Ile Leu Thr Ala Pro Asn
            405                 410                 415

Arg Ser Ser Tyr Arg Tyr Asp Ser Leu Leu Leu Gly Pro Lys Asn Phe
            420                 425                 430

Ser Gly Ile Leu Asp Leu Asp Leu Leu Leu Glu Leu Leu Glu Leu Gln

```
                435             440             445
Glu Arg Leu Arg His Leu Gln Val Trp Ser Pro Glu Ala Gln Arg Asn
450                     455                 460
Ile Ser Leu Gln Asp Ile Cys Tyr Ala Pro Leu Asn Pro Asp Asn Thr
465                     470                  475                 480
Ser Leu Tyr Asp Cys Cys Ile Asn Ser Leu Leu Gln Tyr Phe Gln Asn
                    485                 490                 495
Asn Arg Thr Leu Leu Leu Thr Ala Asn Gln Thr Leu Met Gly Gln
            500                 505                 510
Thr Ser Gln Val Asp Trp Lys Asp His Phe Leu Tyr Cys Ala Asn Ala
            515                 520                 525
Pro Leu Thr Phe Lys Asp Gly Thr Ala Leu Ala Leu Ser Cys Met Ala
            530                 535                 540
Asp Tyr Gly Ala Pro Val Phe Pro Phe Leu Ala Ile Gly Gly Tyr Lys
545                     550                  555                 560
Gly Lys Asp Tyr Ser Glu Ala Glu Ala Leu Ile Met Thr Phe Ser Leu
                    565                 570                 575
Asn Asn Tyr Pro Ala Gly Asp Pro Arg Leu Ala Gln Ala Lys Leu Trp
            580                 585                 590
Glu Glu Ala Phe Leu Glu Glu Met Arg Ala Phe Gln Arg Arg Met Ala
            595                 600                 605
Gly Met Phe Gln Val Thr Phe Met Ala Glu Arg Ser Leu Glu Asp Glu
            610                 615                 620
Ile Asn Arg Thr Thr Ala Glu Asp Leu Pro Ile Phe Ala Thr Ser Tyr
625                     630                  635                 640
Ile Val Ile Phe Leu Tyr Ile Ser Leu Ala Leu Gly Ser Tyr Ser Ser
                    645                 650                 655
Trp Ser Arg Val Met Val Asp Ser Lys Ala Thr Leu Gly Leu Gly Gly
            660                 665                 670
Val Ala Val Val Leu Gly Ala Val Met Ala Ala Met Gly Phe Phe Ser
            675                 680                 685
Tyr Leu Gly Ile Arg Ser Ser Leu Val Ile Leu Gln Val Val Pro Phe
            690                 695                 700
Leu Val Leu Ser Val Gly Ala Asp Asn Ile Phe Ile Phe Val Leu Glu
705                     710                  715                 720
Tyr Gln Arg Leu Pro Arg Arg Pro Gly Glu Pro Arg Glu Val His Ile
                    725                 730                 735
Gly Arg Ala Leu Gly Arg Val Ala Pro Ser Met Leu Leu Cys Ser Leu
            740                 745                 750
Ser Glu Ala Ile Cys Phe Phe Leu Gly Ala Leu Thr Pro Met Pro Ala
            755                 760                 765
Val Arg Thr Phe Ala Leu Thr Ser Gly Leu Ala Val Ile Leu Asp Phe
            770                 775                 780
Leu Leu Gln Met Ser Ala Phe Val Ala Leu Leu Ser Leu Asp Ser Lys
785                     790                  795                 800
Arg Gln Glu Ala Ser Arg Leu Asp Val Cys Cys Cys Val Lys Pro Gln
                    805                 810                 815
Glu Leu Pro Pro Pro Gly Gln Gly Glu Gly Leu Leu Leu Gly Phe Phe
            820                 825                 830
Gln Lys Ala Tyr Ala Pro Phe Leu Leu His Trp Ile Thr Arg Gly Val
            835                 840                 845
Val Leu Leu Leu Phe Leu Ala Leu Phe Gly Val Ser Leu Tyr Ser Met
            850                 855                 860
```

```
Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Val
                885                 890                 895

Gly Ala Pro Val Tyr Phe Val Thr Thr Leu Gly Tyr Asn Phe Ser Ser
            900                 905                 910

Glu Ala Gly Met Asn Ala Ile Cys Ser Ser Ala Gly Cys Asn Asn Phe
            915                 920                 925

Ser Phe Thr Gln Lys Ile Gln Tyr Ala Thr Glu Phe Pro Glu Gln Ser
        930                 935                 940

Tyr Leu Ala Ile Pro Ala Ser Ser Trp Val Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Lys Phe Cys Pro Ser Thr Val Asn Ser Leu Asn Cys Leu Lys Asn
            980                 985                 990

Cys Met Ser Ile Thr Met Gly Ser Val Arg Pro Ser Val Glu Gln Phe
        995                1000                1005

His Lys Tyr Leu Pro Trp Phe Leu Asn Asp Arg Pro Asn Ile Lys
1010                1015                1020

Cys Pro Lys Gly Gly Leu Ala Tyr Ser Thr Ser Val Asn Leu
1025                1030                1035

Thr Ser Asp Gly Gln Val Leu Ala Ser Arg Phe Met Ala Tyr His
1040                1045                1050

Lys Pro Leu Lys Asn Ser Gln Asp Tyr Thr Glu Ala Leu Arg Ala
1055                1060                1065

Ala Arg Glu Leu Ala Ala Asn Ile Thr Ala Asp Leu Arg Lys Val
1070                1075                1080

Pro Gly Thr Asp Pro Ala Phe Glu Val Phe Pro Tyr Thr Ile Thr
1085                1090                1095

Asn Val Phe Tyr Glu Gln Tyr Leu Thr Ile Leu Pro Glu Gly Leu
1100                1105                1110

Phe Met Leu Ser Leu Cys Leu Val Pro Thr Phe Ala Val Ser Cys
1115                1120                1125

Leu Leu Leu Gly Leu Asp Leu Arg Ser Gly Leu Leu Asn Leu Leu
1130                1135                1140

Ser Ile Val Met Ile Leu Val Asp Thr Val Gly Phe Met Ala Leu
1145                1150                1155

Trp Gly Ile Ser Tyr Asn Ala Val Ser Leu Ile Asn Leu Val Ser
1160                1165                1170

Ala Val Gly Met Ser Val Glu Phe Val Ser His Ile Thr Arg Ser
1175                1180                1185

Phe Ala Ile Ser Thr Lys Pro Thr Trp Leu Glu Arg Ala Lys Glu
1190                1195                1200

Ala Thr Ile Ser Met Gly Ser Ala Val Phe Ala Gly Val Ala Met
1205                1210                1215

Thr Asn Leu Pro Gly Ile Leu Val Leu Gly Leu Ala Lys Ala Gln
1220                1225                1230

Leu Ile Gln Ile Phe Phe Phe Arg Leu Asn Leu Leu Ile Thr Leu
1235                1240                1245

Leu Gly Leu Leu His Gly Leu Val Phe Leu Pro Val Ile Leu Ser
1250                1255                1260

Tyr Val Gly Pro Asp Val Asn Pro Ala Leu Ala Leu Glu Gln Lys
1265                1270                1275
```

```
Arg Ala Glu Glu Ala Val Ala Val Met Val Ala Ser Cys Pro
    1280            1285            1290

Asn His Pro Ser Arg Val Ser Thr Ala Asp Asn Ile Tyr Val Asn
    1295            1300            1305

His Ser Phe Glu Gly Ser Ile Lys Gly Ala Gly Ala Ile Ser Asn
    1310            1315            1320

Phe Leu Pro Asn Asn Gly Arg Gln Phe
    1325            1330
```

<210> SEQ ID NO 3
<211> LENGTH: 783
<212> TYPE: DNA
<213> ORGANISM: Homo sapiens
<220> FEATURE:
<221> NAME/KEY: gene
<222> LOCATION: (1)..(783)
<223> OTHER INFORMATION: loop1 (second loop of NPC1L1)

<400> SEQUENCE: 3

```
gtctttacag aactcactac ggaccccgtg gagctgtggt cggcccccaa cagccaagcc    60
cggagtgaga aagcttttcca tgaccagcat ttcggcccct tcttccgaac caaccaggtg   120
atcctgacgg ctcctaaccg gtccagctac aggtatgact ctctgctgct ggggcccaag   180
aacttcagcg gaatcctgga cctggacttg ctgctggagc tgctagagct gcaggagagg   240
ctgcggcacc tccaggtatg gtcgcccgaa gcacagcgca acatctccct gcaggacatc   300
tgctacgccc cctcaatcc ggacaatacc agtctctacg actgctgcat caacagcctc   360
ctgcagtatt tccagaacaa ccgcacgctc ctgctgctca cagccaacca gacactgatg   420
gggcagacct cccaagtcga ctggaaggac cattttctgt actgtgccaa tgccccgctc   480
accttcaagg atggcacagc cctggccctg agctgcatgg ctgactacgg ggcccctgtc   540
ttccccttcc ttgccattgg ggggtacaaa ggaaaggact attctgaggc agaggccctg   600
atcatgacgt tctccctcaa caattaccct gccggggacc ccgtctggc ccaggccaag   660
ctgtgggagg aggccttctt agaggaaatg cgagccttcc agcgtcggat ggctggcatg   720
ttccaggtca cgttcatggc tgagcgctct ctggaagacg agatcaatcg caccacagct   780
gaa                                                                  783
```

<210> SEQ ID NO 4
<211> LENGTH: 261
<212> TYPE: PRT
<213> ORGANISM: Homo sapiens

<400> SEQUENCE: 4

```
Val Phe Thr Glu Leu Thr Thr Asp Pro Val Glu Leu Trp Ser Ala Pro
1               5                   10                  15

Asn Ser Gln Ala Arg Ser Glu Lys Ala Phe His Asp Gln His Phe Gly
                20                  25                  30

Pro Phe Phe Arg Thr Asn Gln Val Ile Leu Thr Ala Pro Asn Arg Ser
            35                  40                  45

Ser Tyr Arg Tyr Asp Ser Leu Leu Leu Gly Pro Lys Asn Phe Ser Gly
        50                  55                  60

Ile Leu Asp Leu Asp Leu Leu Glu Leu Glu Leu Gln Glu Arg
65                  70                  75                  80

Leu Arg His Leu Gln Val Trp Ser Pro Glu Ala Gln Arg Asn Ile Ser
                85                  90                  95

Leu Gln Asp Ile Cys Tyr Ala Pro Leu Asn Pro Asp Asn Thr Ser Leu
```

```
                    100                 105                 110
Tyr Asp Cys Cys Ile Asn Ser Leu Leu Gln Tyr Phe Gln Asn Asn Arg
                115                 120                 125

Thr Leu Leu Leu Leu Thr Ala Asn Gln Thr Leu Met Gly Gln Thr Ser
        130                 135                 140

Gln Val Asp Trp Lys Asp His Phe Leu Tyr Cys Ala Asn Ala Pro Leu
145                 150                 155                 160

Thr Phe Lys Asp Gly Thr Ala Leu Ala Leu Ser Cys Met Ala Asp Tyr
                165                 170                 175

Gly Ala Pro Val Phe Pro Phe Leu Ala Ile Gly Gly Tyr Lys Gly Lys
            180                 185                 190

Asp Tyr Ser Glu Ala Glu Ala Leu Ile Met Thr Phe Ser Leu Asn Asn
                195                 200                 205

Tyr Pro Ala Gly Asp Pro Arg Leu Ala Gln Ala Lys Leu Trp Glu Glu
        210                 215                 220

Ala Phe Leu Glu Glu Met Arg Ala Phe Gln Arg Arg Met Ala Gly Met
225                 230                 235                 240

Phe Gln Val Thr Phe Met Ala Glu Arg Ser Leu Glu Asp Glu Ile Asn
                245                 250                 255

Arg Thr Thr Ala Glu
            260
```

<210> SEQ ID NO 5
<211> LENGTH: 852
<212> TYPE: DNA
<213> ORGANISM: Homo sapiens
<220> FEATURE:
<221> NAME/KEY: gene
<222> LOCATION: (1)..(852)
<223> OTHER INFORMATION: loop of NPC1L1

<400> SEQUENCE: 5

```
atggcggagg ccggcctgag gggctggctg ctgtgggccc tgctcctgcg cttggcccag    60
agtgagcctt acacaaccat ccaccagcct ggctactgcg ccttctatga cgaatgtggg   120
aagaacccag agctgtctgg aagcctcatg acactctcca acgtgtcctg cctgtccaac   180
acgccggccc gcaagatcac aggtgatcac ctgatcctat tacagaagat ctgccccgc   240
ctctacaccg gccccaacac ccaagcctgc tgctccgcca agcagctggt atcactggaa   300
gcgagtctgt cgatcaccaa ggccctcctc acccgctgcc cagcctgctc tgacaatttt   360
gtgaacctgc actgccacaa cacgtgcagc cccaatcaga gcctcttcat caatgtgacc   420
cgcgtggccc agctaggggc tggacaactc ccagctgtgg tggcctatga ggccttctac   480
cagcatagct tgccgagca gagctatgac tcctgcagcc gtgtgcgcgt ccctgcagct   540
gccacgctgg ctgtgggcac catgtgtggc gtgtatggct ctgcccttg caatgcccag   600
cgctggctca acttccaggg agacacaggc aatggtctgg ccccactgga catcaccttc   660
cacctcttgg agcctggcca ggccgtgggg agtgggattc agcctctgaa tgaggggggtt   720
gcacgttgca atgagtccca aggtgacgac gtggcgacct gctcctgcca agactgtgct   780
gcatcctgtc ctgccatagc ccgcccccag gccctcgact ccaccttcta cctgggccag   840
atgccgggca gt                                                       852
```

<210> SEQ ID NO 6
<211> LENGTH: 284
<212> TYPE: PRT
<213> ORGANISM: Homo sapiens

<400> SEQUENCE: 6

```
Met Ala Glu Ala Gly Leu Arg Gly Trp Leu Leu Trp Ala Leu Leu Leu
1               5                   10                  15
Arg Leu Ala Gln Ser Glu Pro Tyr Thr Thr Ile His Gln Pro Gly Tyr
            20                  25                  30
Cys Ala Phe Tyr Asp Glu Cys Gly Lys Asn Pro Glu Leu Ser Gly Ser
        35                  40                  45
Leu Met Thr Leu Ser Asn Val Ser Cys Leu Ser Asn Thr Pro Ala Arg
    50                  55                  60
Lys Ile Thr Gly Asp His Leu Ile Leu Leu Gln Lys Ile Cys Pro Arg
65                  70                  75                  80
Leu Tyr Thr Gly Pro Asn Thr Gln Ala Cys Cys Ser Ala Lys Gln Leu
                85                  90                  95
Val Ser Leu Glu Ala Ser Leu Ser Ile Thr Lys Ala Leu Leu Thr Arg
            100                 105                 110
Cys Pro Ala Cys Ser Asp Asn Phe Val Asn Leu His Cys His Asn Thr
        115                 120                 125
Cys Ser Pro Asn Gln Ser Leu Phe Ile Asn Val Thr Arg Val Ala Gln
    130                 135                 140
Leu Gly Ala Gly Gln Leu Pro Ala Val Val Ala Tyr Glu Ala Phe Tyr
145                 150                 155                 160
Gln His Ser Phe Ala Glu Gln Ser Tyr Asp Ser Cys Ser Arg Val Arg
                165                 170                 175
Val Pro Ala Ala Ala Thr Leu Ala Val Gly Thr Met Cys Gly Val Tyr
            180                 185                 190
Gly Ser Ala Leu Cys Asn Ala Gln Arg Trp Leu Asn Phe Gln Gly Asp
        195                 200                 205
Thr Gly Asn Gly Leu Ala Pro Leu Asp Ile Thr Phe His Leu Leu Glu
    210                 215                 220
Pro Gly Gln Ala Val Gly Ser Gly Ile Gln Pro Leu Asn Glu Gly Val
225                 230                 235                 240
Ala Arg Cys Asn Glu Ser Gln Gly Asp Asp Val Ala Thr Cys Ser Cys
                245                 250                 255
Gln Asp Cys Ala Ala Ser Cys Pro Ala Ile Ala Arg Pro Gln Ala Leu
            260                 265                 270
Asp Ser Thr Phe Tyr Leu Gly Gln Met Pro Gly Ser
        275                 280
```

<210> SEQ ID NO 7
<211> LENGTH: 30
<212> TYPE: DNA
<213> ORGANISM: Homo sapiens
<220> FEATURE:
<221> NAME/KEY: gene
<222> LOCATION: (1)..(30)
<223> OTHER INFORMATION: loop of NPC1L1

<400> SEQUENCE: 7
ggcttcttct cctacttggg tatccgctcc                                  30

<210> SEQ ID NO 8
<211> LENGTH: 10
<212> TYPE: PRT
<213> ORGANISM: Homo sapiens

<400> SEQUENCE: 8

```
Gly Phe Phe Ser Tyr Leu Gly Ile Arg Ser
1               5                   10
```

<210> SEQ ID NO 9
<211> LENGTH: 42
<212> TYPE: DNA
<213> ORGANISM: Homo sapiens
<220> FEATURE:
<221> NAME/KEY: gene
<222> LOCATION: (1)..(42)
<223> OTHER INFORMATION: loop of NPC1L1

<400> SEQUENCE: 9

```
accccccatgc cagctgtgcg gacctttgcc ctgacctctg gc                          42
```

<210> SEQ ID NO 10
<211> LENGTH: 14
<212> TYPE: PRT
<213> ORGANISM: Homo sapiens

<400> SEQUENCE: 10

Thr Pro Met Pro Ala Val Arg Thr Phe Ala Leu Thr Ser Gly
1               5                   10

<210> SEQ ID NO 11
<211> LENGTH: 744
<212> TYPE: DNA
<213> ORGANISM: Homo sapiens
<220> FEATURE:
<221> NAME/KEY: gene
<222> LOCATION: (1)..(744)
<223> OTHER INFORMATION: loop of NPC1L1

<400> SEQUENCE: 11

```
tgccacatca gcgtgggact ggaccaggag ctggccctgc ccaaggactc gtacctgctt        60
gactatttcc tctttctgaa ccgctacttc gaggtggggg ccccggtgta ctttgttacc      120
accttgggct acaacttctc cagcgaggct gggatgaatg ccatctgctc cagtgcaggc      180
tgcaacaact tctccttcac ccagaagatc cagtatgcca cagagttccc tgagcagtct      240
tacctggcca tccctgcctc ctcctggggtg gatgacttca ttgactggct gaccccgtcc      300
tcctgctgcc gcctttatat atctggcccc aataaggaca gttctgccc ctcgaccgtc        360
aactctctga actgcctaaa gaactgcatg agcatcacga tgggctctgt gaggccctcg      420
gtggagcagt ccataagta tcttccctgg ttcctgaacg accggcccaa catcaaatgt      480
cccaaaggcg gcctggcagc atacagcacc tctgtgaact tgacttcaga tggccaggtt      540
ttagcctcca ggttcatggc ctatcacaag cccctgaaaa actcacagga ttacacagaa      600
gctctgcggg cagctcgaga gctggcagcc aacatcactg ctgacctgcg gaaagtgcct      660
ggaacagacc cggcttttga ggtcttcccc tacacgatca ccaatgtgtt ttatgagcag      720
tacctgacca tcctccctga gggg                                              744
```

<210> SEQ ID NO 12
<211> LENGTH: 248
<212> TYPE: PRT
<213> ORGANISM: Homo sapiens

<400> SEQUENCE: 12

Cys His Ile Ser Val Gly Leu Asp Gln Glu Leu Ala Leu Pro Lys Asp
1               5                   10                  15

Ser Tyr Leu Leu Asp Tyr Phe Leu Phe Leu Asn Arg Tyr Phe Glu Val
                20                  25                  30

Gly Ala Pro Val Tyr Phe Val Thr Thr Leu Gly Tyr Asn Phe Ser Ser
            35                  40                  45

```
Glu Ala Gly Met Asn Ala Ile Cys Ser Ser Ala Gly Cys Asn Asn Phe
 50                  55                  60

Ser Phe Thr Gln Lys Ile Gln Tyr Ala Thr Glu Phe Pro Glu Gln Ser
 65                  70                  75                  80

Tyr Leu Ala Ile Pro Ala Ser Ser Trp Val Asp Asp Phe Ile Asp Trp
                 85                  90                  95

Leu Thr Pro Ser Ser Cys Cys Arg Leu Tyr Ile Ser Gly Pro Asn Lys
            100                 105                 110

Asp Lys Phe Cys Pro Ser Thr Val Asn Ser Leu Asn Cys Leu Lys Asn
        115                 120                 125

Cys Met Ser Ile Thr Met Gly Ser Val Arg Pro Ser Val Glu Gln Phe
130                 135                 140

His Lys Tyr Leu Pro Trp Phe Leu Asn Asp Arg Pro Asn Ile Lys Cys
145                 150                 155                 160

Pro Lys Gly Gly Leu Ala Ala Tyr Ser Thr Ser Val Asn Leu Thr Ser
                165                 170                 175

Asp Gly Gln Val Leu Ala Ser Arg Phe Met Ala Tyr His Lys Pro Leu
            180                 185                 190

Lys Asn Ser Gln Asp Tyr Thr Glu Ala Leu Arg Ala Ala Arg Glu Leu
        195                 200                 205

Ala Ala Asn Ile Thr Ala Asp Leu Arg Lys Val Pro Gly Thr Asp Pro
210                 215                 220

Ala Phe Glu Val Phe Pro Tyr Thr Ile Thr Asn Val Phe Tyr Glu Gln
225                 230                 235                 240

Tyr Leu Thr Ile Leu Pro Glu Gly
                245

<210> SEQ ID NO 13
<211> LENGTH: 21
<212> TYPE: DNA
<213> ORGANISM: Homo sapiens
<220> FEATURE:
<221> NAME/KEY: gene
<222> LOCATION: (1)..(21)
<223> OTHER INFORMATION: loop of NPC1L1

<400> SEQUENCE: 13
tggggcatca gttacaatgc t                                            21

<210> SEQ ID NO 14
<211> LENGTH: 7
<212> TYPE: PRT
<213> ORGANISM: Homo sapiens

<400> SEQUENCE: 14

Trp Gly Ile Ser Tyr Asn Ala
 1               5

<210> SEQ ID NO 15
<211> LENGTH: 12
<212> TYPE: DNA
<213> ORGANISM: Homo sapiens
<220> FEATURE:
<221> NAME/KEY: gene
<222> LOCATION: (1)..(12)
<223> OTHER INFORMATION: loop of NPC1L1

<400> SEQUENCE: 15
cgcctcaacc tc                                                      12
```

```
<210> SEQ ID NO 16
<211> LENGTH: 4
<212> TYPE: PRT
<213> ORGANISM: Homo sapiens

<400> SEQUENCE: 16

Arg Leu Asn Leu
1
```